United States Patent [19]
Tekulve

[11] Patent Number: 6,117,157
[45] Date of Patent: Sep. 12, 2000

[54] HELICAL EMBOLIZATION COIL

[75] Inventor: Kurt J. Tekulve, Ellettsville, Ind.

[73] Assignee: Cook Incorporated, Bloomington, Ind.

[21] Appl. No.: 09/139,494

[22] Filed: Aug. 25, 1998

Related U.S. Application Data

[63] Continuation-in-part of application No. 08/609,767, Feb. 23, 1996, Pat. No. 5,797,953, which is a continuation of application No. 08/507,600, Jul. 26, 1995, abandoned, which is a continuation of application No. 08/210,798, Mar. 18, 1994, abandoned.

[51] Int. Cl.$^7$ .................................................. A61B 17/00
[52] U.S. Cl. .............................................. 606/200; 606/1
[58] Field of Search .............................. 606/1, 191, 194, 606/195, 198, 200; 623/1; 128/899

[56] References Cited

U.S. PATENT DOCUMENTS

| | | |
|---|---|---|
| 4,706,671 | 11/1987 | Weinrib . |
| 4,994,069 | 2/1991 | Ritchart et al. . |
| 5,108,407 | 4/1992 | Geremia et al. . |
| 5,108,420 | 4/1992 | Marks . |
| 5,122,136 | 6/1992 | Guglielmi et al. . |

(List continued on next page.)

FOREIGN PATENT DOCUMENTS

| | | |
|---|---|---|
| 3203410 | 11/1982 | Germany . |
| 1771719 | 10/1992 | U.S.S.R. . |
| 9216163 | 10/1992 | WIPO . |
| 9407560 | 4/1994 | WIPO . |
| 9409705 | 5/1994 | WIPO . |

OTHER PUBLICATIONS

Cook Incorporated, "Hilal Embolization Microcoils," Bloomington, Indiana, 1988.

Cragg, Andrew et al., "A New Percutaneous Vena Cave Filter", *AJR* 141, Sep. 1983.

*Primary Examiner*—Gary Jackson
*Assistant Examiner*—William W. Lewis
*Attorney, Agent, or Firm*—Richard J. Godlewski

[57] ABSTRACT

A conically helically shaped embolization coil (10) for occluding a blood vessel, aneurysm, and the like. The embolization coil includes a continuous platinum-tungsten alloy wire strand (11) wound into a longitudinally extending coil (12) having a plurality of tightly spaced turns (13). The longitudinally extending coil is wound into a conically helically shaped coil (15) with a plurality of radially expanding turns (16). Distal turn (17) of the radially expanding turns has a minor diameter (18) less than a minimum diameter (34) of a vessel (32) of which the embolization is to be positioned therein. Uncompressed proximal turn (19) of the radially expanding turns has a major diameter (20) greater than a maximum diameter (33) of the vessel in which the coil to be positioned. The coil is stress relieved and, in particular, heat treated by heating the coil to a stress relief temperature of the continuous wire strand and cooled to relieve residual stresses formed during the winding of the coil and to minimize the formation of new residual stresses formed during the cool down period of the heat treatment. Thrombogenic fibers (26) are positioned in the tightly spaced turns of the coil to attract thrombus and build up a mass that occludes the vessel lumen. The embolization coil (10) can also include first and second conically helically shaped coils (15, 45) that expand radially in generally opposite directions. The multiple helically shaped coils (15, 45) of the embolization coil accurately and centrally position the embolization coil in the vessel. Each coil acts as an anchor for the other to cause the turns of the coil to make longitudinal contact with each other regardless of the direction of blood flow thereagainst. The longitudinally extending coil (12) of the embolization coil (10) can also be formed to include distal and proximal end turns extending longitudinally from the conically helically shaped coil (15) to better affix and centrally position the embolization coil at the occlusion site.

20 Claims, 5 Drawing Sheets

U.S. PATENT DOCUMENTS

| | | |
|---|---|---|
| 5,133,709 | 7/1992 | Prince . |
| 5,133,731 | 7/1992 | Butler et al. . |
| 5,167,624 | 12/1992 | Butler et al. . |
| 5,190,546 | 3/1993 | Jervis . |
| 5,192,301 | 3/1993 | Kamiya et al. . |
| 5,217,484 | 6/1993 | Marks . |
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,267,955 | 12/1993 | Hanson . |
| 5,304,194 | 4/1994 | Chee et al. . |
| 5,522,822 | 6/1996 | Phelps et al. . |
| 5,540,680 | 7/1996 | Guglielmi et al. . |

HELICAL EMBOLIZATION COIL

RELATED APPLICATIONS

This is a continuation-in-part of application Ser. No. 08/609,767 filed Feb. 23, 1996; now U.S. Pat. No. 5,797,953 which is a continuation of application Ser. No. 08/507,600, filed Jul. 26, 1995, now abandoned; which is a file wrapper continuation of application Ser. No. 08/210,798, filed Mar. 18, 1994, now abandoned.

TECHNICAL FIELD

This invention relates generally to embolization coils and, in particular, to an embolization coil that is conically helically shaped.

BACKGROUND OF THE INVENTION

Intravascular interventional procedures for providing an artificial embolism are desirable in some patients for controlling internal bleeding, preventing blood supply to tumors, or relieving pressure in the vessel wall near an aneurysm. Several approaches are known for providing an artificial embolism, including the use of an inflatable, detachable balloon or the injection of a coagulative substance. Another approach utilizes an occlusive wire coil and delivery system for positioning the coil at a desirable site in a blood vessel.

One wire coil and delivery system includes a flexible, coiled wire that when released from the distal end of a delivery catheter assumes a randomly coiled, space-filling mass. The wire is released from the catheter by a pusher catheter with a closed distal end for engaging the proximal end of the coil. A problem with this system is that the wire coil is just pushed out the distal end of the delivery catheter toward the target embolism site and then assumes a folded, convoluted configuration. This folded, convoluted configuration is obtained with the use of an occlusion wire that possesses memory which returns the wire from a stretched to a relaxed convoluted condition. One problem with this convoluted configuration coil is that precise positioning of the coil at the occlusion site is difficult to obtain. This is mainly due to the coiled configuration of the wire in which the distal end of the convoluted wire engages the wall of the vessel and longitudinally displaces the delivery catheter. As a result, the delivery catheter and occlusion coil are proximally displaced from the desired occlusion site. Such longitudinal displacement can readily prevent an aneurysm from being occluded. Furthermore, the displaced convoluted coil, which is to be positioned in, for example, an aneurysm, then proceeds downstream and causes an occlusion at an undesired site. This can cause additional pressure to be applied to the already weakened wall of the aneurysm.

Another problem with this convoluted coil is ensuring that sufficient mass is positioned across the cross-sectional area of the vessel lumen to sufficiently restrict blood flow.

SUMMARY OF THE INVENTION

The foregoing problems are solved and a technical advance is achieved in an illustrative embolization coil that is conically helically shaped with a plurality of radially expanding turns. The distal turn of the radially expanding turns has a minor diameter less than the minimum diameter of a vessel in which the embolization coil is to be positioned. This advantageously allows for precise positioning of the coil at the embolization site. The distal end of the coil is introduced from a delivery catheter into the central region of the vessel without longitudinally displacing the delivery catheter from the occlusion site. As the proximal radially increasing turns of the coil expand against the interior surface of the vessel wall, the embolization coil is fixedly positioned in the vessel with the longitudinal axis of the coil being substantially aligned with that of the vessel lumen. The uncompressed proximal turn of the coil has a major diameter greater than the maximum diameter of the vessel to advantageously expand against the interior surface of the vessel wall. As a result, the conically helically shaped coil is fixedly and precisely positioned in the vessel at the occlusion site. Furthermore, the radially expanding coil turns effectively covers the cross-sectional area of the vessel lumen, thus significantly reducing blood flow through the coil.

To further occlude the vessel, the embolization coil includes a continuous wire strand that is wound into a longitudinally extending coil with a plurality of tightly spaced turns. Thrombogenic fibers are positioned in the tightly spaced turns of the longitudinally extending coil to further attract thrombus thereto and quickly build up a mass that completely occludes the vessel.

To centrally position the embolization coil in substantial alignment with the longitudinal axis of the vessel lumen, the radially expanding turns of the conically helically shaped coil include spacing that increases proximally. This advantageously allows the embolization coil to be precisely and fixedly positioned at the occlusion site. The thrombogenic fibers positioned along the length of the coil and the proximally increasing turns also quickly build up a mass for occlusion of the vessel lumen.

For advantageously maintaining the conical helical shape of the coil, the continuous wire strand is stress relieved and, in particular, heat treated after the longitudinally extending coil is wound into a conical helical shape. The heat treatment advantageously relieves stresses that are formed when winding the longitudinally extending coil and the conically helically shaped coil. The heat treatment process includes heating the embolization coil at a stress relief temperature of the continuous wire strand for a first time period to relieve the residual stresses, and then gradually cooling down the coil from the stress relief temperature for a second time period greater than the first to minimize the introduction of new residual stresses during the cool down. Preferably, the continuous wire strand comprises a metallic alloy material, such as a platinum-tungsten alloy, that is substantially free of surface oxidation, which is considered a blood contaminant.

The conically helically shaped coil is formed by winding the longitudinally extending coil around a longitudinally tapered mandril with a plurality of minimally spaced turns. The mandril advantageously comprises a stainless steel material to minimize the formation of surface oxidation thereon during the heat treatment process. The metallic alloy material of the coil can also comprise at least one from a group consisting of platinum, stainless steel, iridium, palladium, tungsten, and gold. When wound around the tapered mandril, the coil is heated at the stress relief temperature of the metallic alloy and then cooled. The conically helically shaped coil is removed from the mandril, at which time the spacing between the radially expanding turns increases proximally from the distal end thereof. The embolization coil is then positioned in a cannula in which the coil is positioned therein in a delivery state for insertion into a guiding or delivery catheter.

In another illustrative embodiment of the embolization coil of the present invention, the embolization coil includes first and second conically helically shaped coils having first and second pluralities of radially expanding turns that expand in generally opposite directions. This configuration advantageously better orients the embolization coil along the longitudinal axis of the vessel in which the embolization coil is to be positioned. Furthermore, each plurality of expanding turns provides an anchor for the other so that the radially expanding turns longitudinally contact each other in response to blood flowing in either direction in the vessel to be occluded. With an embolization coil having only one plurality of radially expanding turns, blood flowing into the conically helically shaped coil would simply expand the spacing between the turns and inhibit occlusion of the vessel. In this embodiment utilizing first and second pluralities of radially expanding turns, blood or fluid flowing in either direction in the vessel causes the radially expanding turns of each plurality to longitudinally contact each other in response to fluid flow and thereby vastly improve the occlusion process in the vessel.

This embolization coil including first and second pluralities of radially expanding turns is formed by winding a longitudinally extending coil around a longitudinally tapered mandril that increases in diameter in opposite longitudinal directions. The first and second conically helically shaped coils are heated at a temperature so as to advantageously relieve the stresses thereof and then cooling the coils for a greater time period than that of the heating period so as to conform the coils to the shape of the longitudinally tapered mandril. As a result, the conically helically shaped coils are heat treated to release stresses that are formed when winding the longitudinally extending coil and the first and the second conically helically shaped coils. To advantageously prevent surface contamination of the embolization coil, the longitudinally tapered mandril includes the selection of a material that remains substantially free of surface oxidation during heating and cooling of the conically helically shaped coils.

The wire strand of this embolization coil comprises a metallic alloy from at least one from a group consisting of platinum, stainless steel, iridium, palladium, tungsten, and gold. This selection of the metallic alloy minimizes surface contamination of the embolization coil. In another aspect, the wire strand includes a metallic material that is substantially free of surface oxidation.

To further enhance vessel occlusion, the embolization coil further includes thrombogenic fibers that are positioned in the tightly spaced turns of the longitudinally extending coil.

In yet another alternative embodiment of the present invention, the embolization coil includes a conically helically shaped coil having radially expanding turns that expand in a first direction. The longitudinally extending coil of the embolization coil is also wound into at least one end turn that extends from the minor diameter distal turn of the radially expanding turns in a second direction that is generally opposite to the first direction. This end turn has an end diameter larger than that of the minor diameter of the distal turn of the radially expanding turns. As with the other embodiments of the embolization coil, the radially expanding turns longitudinally contact each other in response to blood flowing therethrough to occlude a site in which the embolization coil is positioned. A further advantage of this alternative embodiment of the embolization coil is that the larger diameter end turn can be used to anchor the coil at a site such as an atrial septum defect. The larger diameter end turn and the larger turns of the conically helically shaped coil prevent migration of the coil through the defect and allow occlusion of the defect to occur when the turns of the conically helically shaped coil contact each other in response to blood flowing thereagainst.

In still yet another alternative embodiment of the present invention, the embolization coil includes a conically helically shaped coil having a plurality of radially expanding turns. The longitudinally extending coil of the embolization coil is also wound into at least one proximal end turn extending from the proximal turn of the conically helically shaped coil. The diameter of this end turn is no greater than that of the major diameter of the conically helically shaped coil. As a result, one or more of these proximal end turns advantageously further anchor the embolization coil at the occlusion site so as to prevent migration of the embolization coil during placement at and occlusion of the site.

BRIEF DESCRIPTION OF THE DRAWINGS

FIG. 11 depicts yet another alternative embodiment of the present invention in which the embolization coil includes a proximal end turn extending longitudinally from the proximal turn of the conically helically shaped coil at a diameter no greater than the major diameter of the conically helically shaped coil.

DETAILED DESCRIPTION

Figure 1:
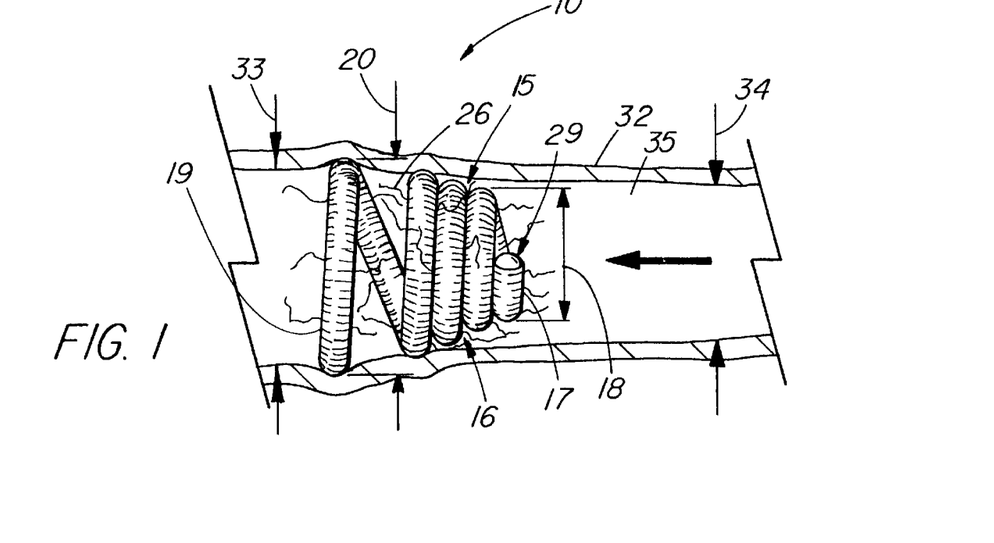
FIG. 1 depicts an illustrative conically helically shaped embolization coil of the present invention longitudinally positioned in the vessel of a patient.

FIG. 1 depicts illustrative embolization coil 10 longitudinally positioned in vessel 32 of a human or animal body. The embolization coil has been formed into conically helically shaped coil 15 having a longitudinal axis that is substantially aligned with the longitudinal axis of vessel 32.

The conically helically shaped coil has a plurality of radially expanding turns 16 with thrombogenic fibers 26 spaced at predetermined intervals along the length of the coil. The conically helically shaped coil extends over almost the entire cross-sectional area of vessel lumen 35 to substantially impede blood flow and attract thrombus. The thrombogenic fibers of the embolization coil more readily attract thrombus to further build up a mass that entirely occludes the vessel.

Due to the build up of plaque and other irregularities in the vessel wall, lumen 35 has a maximum diameter 33 and a minimum diameter 34 through any given length of the vessel. To ensure longitudinal alignment and fixed positioning of the embolization coil in the vessel lumen, distal turn 17 of coil 15 has a minor diameter 18 that is less than minimum diameter 34 of the vessel, and compressed proximal turn 19 of coil 15, when in an uncompressed condition, has a major diameter 20 that is greater than maximum diameter 33 of the vessel. This sizing of the conically helically shaped coil ensures that distal end 29 of the coil is introduced from a delivery catheter into the central region of the vessel. The successive turns of the coil radially increase in size as the embolization coil is released from the delivery catheter to engage and expand against the interior surface or intimal layer of the vessel wall. As a result, minor diameter distal turn 17 does not engage the vessel wall and longitudinally displace the delivery catheter positioned at the occlusion site. The proximal radially expanding turns of the coil centrally and longitudinally position the coil in the vessel lumen. Furthermore, the most proximal turns of the coil readily expand against the interior surface of the vessel wall and fixedly position the coil at the desired occlusion site. Precision positioning of the coil is thus readily achieved without concern for the embolization coil emerging from the delivery catheter and tumbling or drifting to an undesired occlusion site in the vessel.

Figure 2:
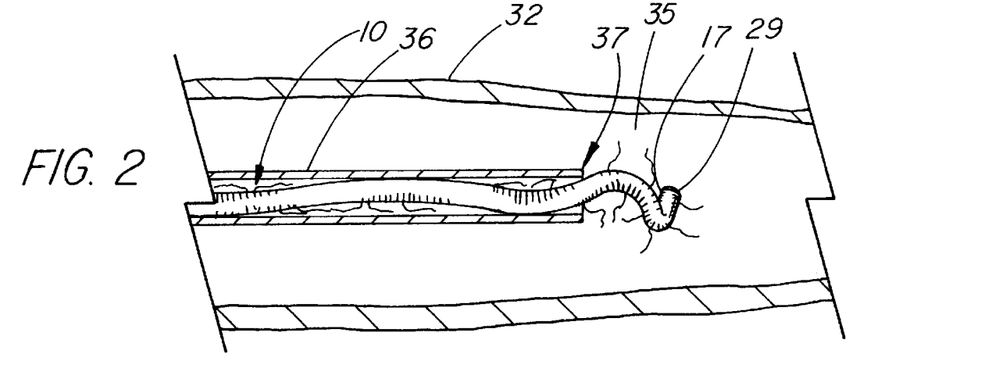
FIG. 2 depicts the distal turn of the embolization coil of FIG. 1 emerging from the distal end of a delivery catheter.

FIG. 2 depicts embolization coil 10 of FIG. 1 positioned in a stretched or loaded condition in delivery catheter 36 and distal end 29 of turn 17 of the coil emerging from distal end 37 of the catheter. Distal end 29 of the coil is centrally positioned in vessel lumen 35 with distal turn 17 emerging from the delivery catheter. As a result, distal end 29 of the coil as well as distal turn 17 is introduced into the vessel lumen without longitudinally displacing delivery catheter 36 from the occlusion site in vessel 32.

Figure 3:
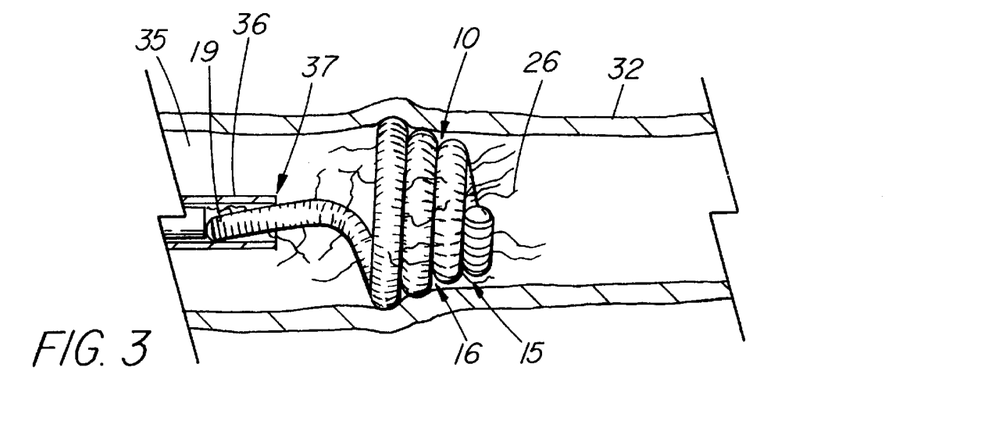
FIG. 3 depicts the embolization coil of FIG. 1 emerging from the distal end of a delivery catheter with only the proximal turn remaining in the delivery catheter.

FIG. 3 depicts embolization coil 10 of FIG. 1 emerging from distal end 37 of delivery catheter 36 in vessel lumen 35 with only proximal turn 19 remaining in the delivery catheter. As shown, the proximal radially expanding turns 16 of conically helically shaped coil 15 have emerged from the delivery catheter and expanded to compress against the interior surface of the vessel wall. As a result, the longitudinal axis of the conically helically shaped coil is centrally positioned in vessel lumen 35 and aligned with the longitudinal axis of the vessel. Furthermore, the introduction of the embolization coil at the occlusion site is accomplished without longitudinally displacing the delivery catheter or allowing the coil to flow or tumble in the blood stream to an undesired occlusion site. Additionally, the radially expanding turns accurately and securely position the embolization coil at the occlusion site in the vessel. When the embolization coil is fully released from the delivery catheter, the radially expanding turns of the coil extend almost over the entire cross-sectional area of the vessel lumen. This significantly reduces blood flow and further promotes thrombus formation on the coil and thrombogenic fibers 26 extending from the coil.

Figure 4:
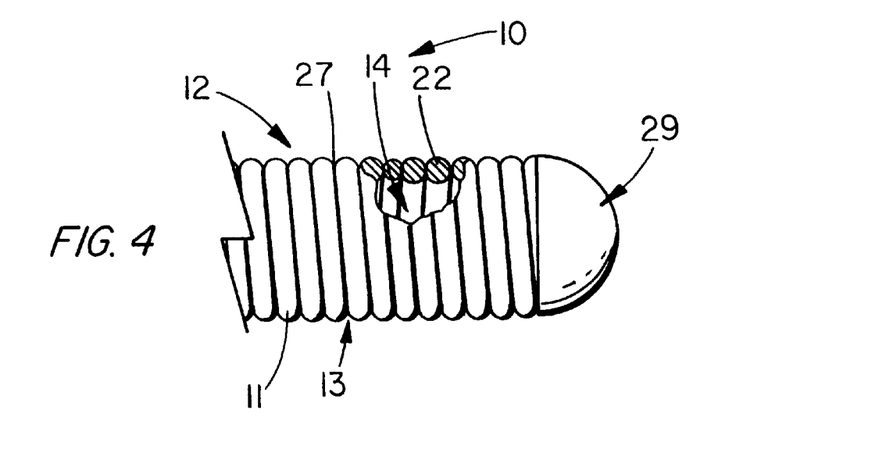
FIG. 4 depicts a partially sectioned view of the embolization coil of FIG. 1 in an elongated condition prior to being wound into a conically helically shaped coil.

FIG. 4 depicts a partially sectioned view of embolization coil 10 of FIG. 1 in an elongated condition prior to being wound into a conically helically shaped coil. The embolization coil comprises continuous wire strand 11 that has been wound in a well-known manner into longitudinally extending coil 12 with a plurality of tightly spaced turns 13 and hollow passage 14 extending longitudinally therein. Continuous wire strand 11 comprises a metallic alloy material 22 that is substantially free of surface oxidation that is considered an undesired contaminant in the bloodstream of a patient. Preferably, the continuous wire strand comprises a commercially available 0.003" diameter platinum wire with 8 percent tungsten. Other alternative alloys include well-known medical grade stainless steel along with alloys including at least one from a group consisting of platinum, iron, iridium, palladium, tungsten, and gold. These particular alloys exhibit extremely low levels of surface oxidation particularly when heat treated to relieve residual stresses formed during the winding of the embolization coil. Additionally, these metallic alloys are also considered thrombogenic to further promote thrombus formation and occlusion of the vessel at the occlusion site. The continuous wire strand is preferably wound into a longitudinally extending coil approximately 6 cm long with a 0.014" outside diameter and tightly spaced turns with minimal, if any, spacing 27 therebetween. Distal end 29 of the longitudinally extending coil is soldered or welded to present a rounded or smooth surface, which will not catch on the interior surface of the guiding catheter.

Figure 5:
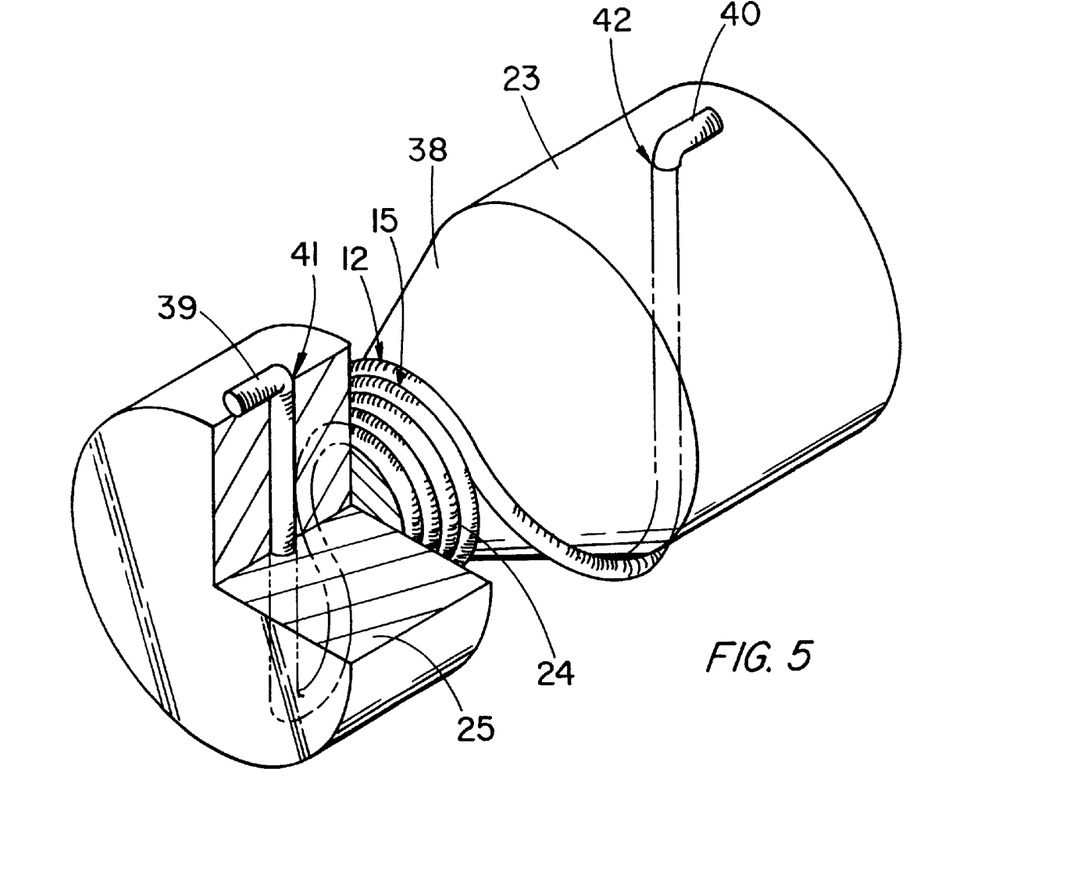
FIG. 5 depicts the longitudinally extending coil of FIG. 4 wound around the tapered surface of a mandril to form a conically helically shaped coil.

FIG. 5 depicts longitudinally extending coil 12 of FIG. 4 wound around longitudinally tapered surface 38 of mandril 23 to form conically helically shaped coil 15 with minimally spaced turns 24. Ends 39 and 40 of the longitudinally extending coil are positioned through respective transverse mandril holes 41 and 42 and bent to fixedly position the coil around longitudinally tapered surface 38. The outside diameter of mandril 23 preferably ranges from 0.250" to 0.325" with longitudinally tapered surface 38 necking down to a minimum diameter of 0.030" to 0.035". As a result, longitudinally tapered surface forms an angle with the longitudinal axis of the mandril of approximately 41 to 46 degrees. Since the wire strand and mandril are heat treated, mandril 23 comprises material 25 such as stainless steel that is heat treated in an oxygen free oven or another metal such as titanium or a metallic alloy that exhibits extremely low levels of surface oxidation after being heat treated. As suggested, the stainless steel mandril is placed in an oxygen free oven such as a commercially available argon oven to minimize surface oxidation during the heat treatment process.

Longitudinally extending coil 12 wound around longitudinally tapered mandril 23 to form conically helically shaped coil 15 is stress relieved and, in particular, heat treated to relieve residual stresses that formed during winding of the embolization coil. In particular, these residual stresses are formed when continuous wire strand 11 is wound into longitudinally extending coil 12 and, more importantly, when longitudinally extending coil 12 is wound around tapered mandril 23 to form conically helically shaped coil 15. By way of example, the longitudinally extending coil 12 and tapered stainless steel mandril 23 are positioned in a commercially available argon oven to minimize the formation of surface oxidation particularly on the stainless steel mandril during the heat treatment process. The coil and mandril are heated in the oven to a stress relief temperature of the platinum-tungsten alloy of approximately 1,012 degrees Fahrenheit for a first time period of approximately 2 hours to relieve stresses formed during the winding of the coil. The heated coil and mandril are then cooled down from this stress relief temperature for a second time period of, for example, 8 hours, which is much greater than the first 2-hour time period. This gradual cool down period minimizes the formation of new residual stresses that can be formed when the coil is cooled down too quickly.

As was previously suggested, the material of the embolization coil as well as that of the mandril is selected to be substantially free of surface oxidation that can be readily formed during the heating and cooling of the coil and mandril in the oven. The formation of surface oxidation is a concern, since it is considered a contaminant when introduced into the bloodstream of a patient. After the coil and mandril are stress relieved, conically helically shaped coil 15 is removed from the mandril. Although the coil has been stress relieved and, in particular, heat treated, minimally spaced turns 24 of the coil on the mandril expand to a spacing that increases proximally from the distal end of the coil.

Figure 6:
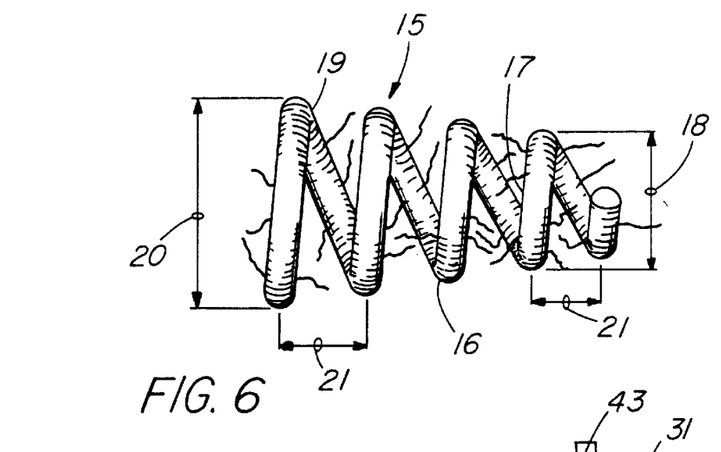
FIG. 6 depicts the conically helically shaped coil of FIG. 5 after it has been removed from the mandril.

FIG. 6 depicts conically helically shaped coil 15 of FIG. 5 after it has been removed from the mandril. The conically helically shaped coil has a plurality of radially expanding turns 16 with spacing 21 that increases proximally from distal turn 17 to proximal turn 19. As previously indicated, distal turn 17 has minor diameter 18, whereas proximal turn 19 has major diameter 20. Spacing 21 between radially expanding turns 16 is typically no more than 2 mm in width at distal turn 17 and increases proximally to a maximum spacing of 5 mm at proximal turn 19.

Figure 7:
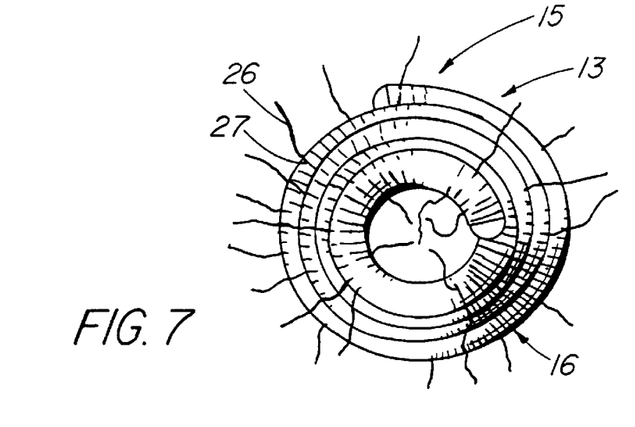
FIG. 7 depicts an end view of the conically helically shaped coil of FIG. 6.

FIG. 7 depicts an end view of conically helically shaped coil 15 of FIG. 6. Radially expanding turns 16 of the coil are readily observed from this end view. Thus, it can be more readily appreciated how the radially expanding turns of the embolization coil nearly cover the entire cross-sectional area of a vessel lumen. Thrombogenic fibers of, for example, commercially available 0.00075" diameter Z-twist, DACRON fiber material are placed at periodic intervals along the length of the coil in minimal spacing 27 between tightly spaced turns 13 of the longitudinally extending coil.

Figure 8:
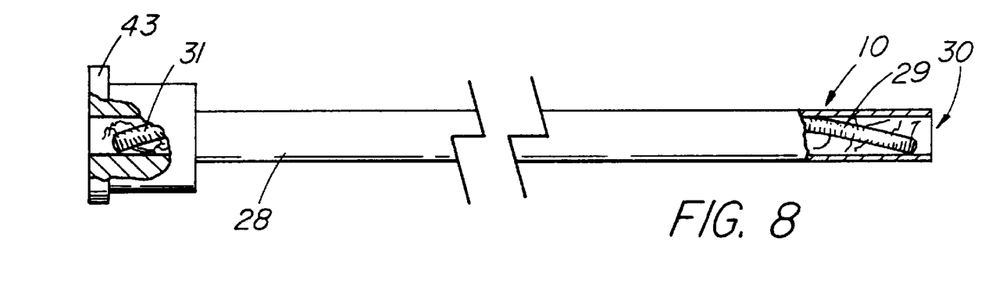
FIG. 8 depicts a partially sectioned view of a shipping cannula with the embolization coil of the present invention positioned therein.

FIG. 8 depicts a partially sectioned view of shipping cannula 28 with embolization coil 10 inserted therein in a stretched condition. By way of example, the shipping cannula is a 21 gauge thin wall stainless steel tube with Luer-lock fitting 43 at the proximal end thereof. The embolization coil is positioned in this cannula for introduction into a guiding or delivery catheter for introduction at the occlusion site. Normally, the guiding or delivery catheter is percutaneously positioned at the occlusion site. The embolization coil is then transferred from the shipping cannula into the delivery catheter with an introducer stylet that is inserted through the proximal end of the shipping cannula and into the passage of the delivery catheter. To ensure proper placement of the embolization coil, distal end 29 of the embolization coil is positioned proximate distal end 30 of the shipping cannula with proximal end 31 positioned proximate the proximal end of the cannula.

Figure 9:
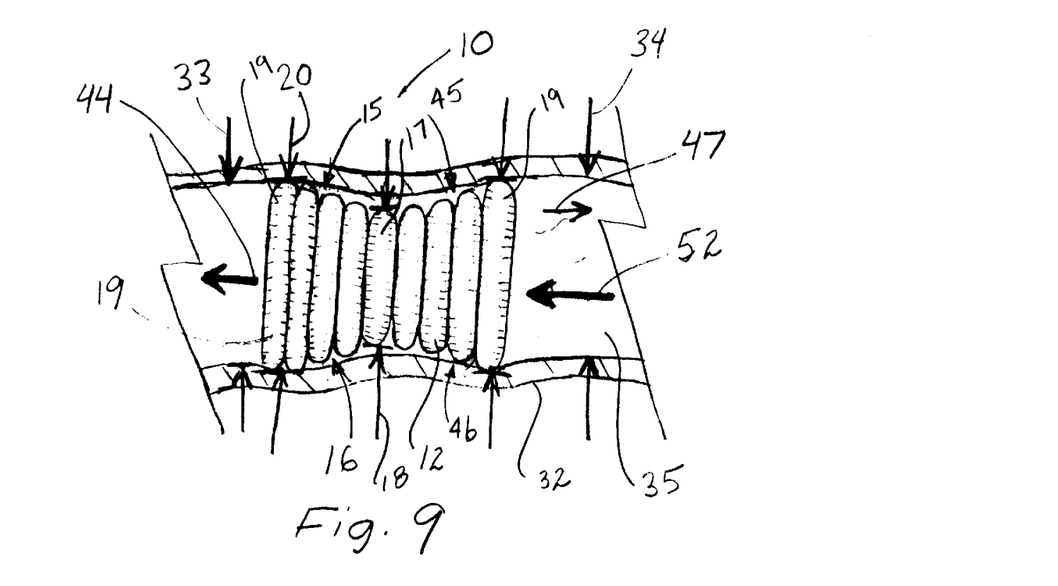
FIG. 9 depicts an alternative embodiment of the present invention in which the embolization coil includes first and second conically helically shaped coils expanding in generally opposite directions.

FIG. 9 depicts an alternative embodiment of the present invention in which the embolization coil 10 includes first and second conically helically shaped coils 15 and 45 expanding in generally opposite directions 44 and 47 in vessel 32 of a patient. As previously described with respect to FIG. 4, this embodiment of embolization coil 10 also includes a continuous wire strand 11 that has been wound in a well-known manner into longitudinally extending coil 12 with a plurality of tightly spaced turns 13 and hollow passage 14 extending longitudinally therein. Continuous wire strand 11 comprises a metallic alloy material 22 that is substantially free of surface oxidation. Preferably, the metallic alloy is platinum with eight percent tungsten formed in commercially available 0.003" diameter wire. Other alternative alloys or metallic material 22 include well-known medical grade stainless steel along with metallic alloys including at least one from a group consisting of platinum, iridium, palladium, tungsten, and gold.

Longitudinally extending coil 12 of the embolization coil is wound into first and second conically helically shaped coils 15 and 45. The first conically helically shaped coil 15 includes a plurality of radially expanding turns 16 that expand in a first direction indicated by arrow 44. The second conically helically shaped coil 45 includes a plurality of radially expanding turns 46 that expand in a second direction indicated by arrow 47. First and second directions 44 and 47 are generally opposite each other.

Vessel lumen 35 has a maximum diameter 33 and a minimum diameter 34 at any given length of the vessel. To help ensure longitudinal alignment and fixed positioning of the embolization coil in the vessel lumen, minimum diameter turn 17 of coils 15 and 45 has a minor diameter 18 that is less than minimum diameter 34 of the vessel. Compressed maximum diameter turn 19 of coils 15 and 45, when in an uncompressed condition, has a major diameter 20 that is greater than maximum diameter 33 of the vessel. This sizing of the conically helically shaped coils ensures accurate positioning of the embolization coil as it is introduced into the vessel. The successive turns of the two coils readily decrease in size toward the middle of the embolization coil. As a result, blood flow in either direction in the vessel causes the turns of the first and second conically helically shaped coils to longitudinally contact each other and occlude the vessel. Regardless of blood flow direction, one conically helically shaped coil acts as an anchor or stationary base for the turns of the other coil to make longitudinal contact with each other in response to blood flow thereagainst. The larger diameter end turns 19 of the conically helically shaped coils 15 and 45 solidly anchor and centrally align the embolization coil in the vessel.

Figure 12:
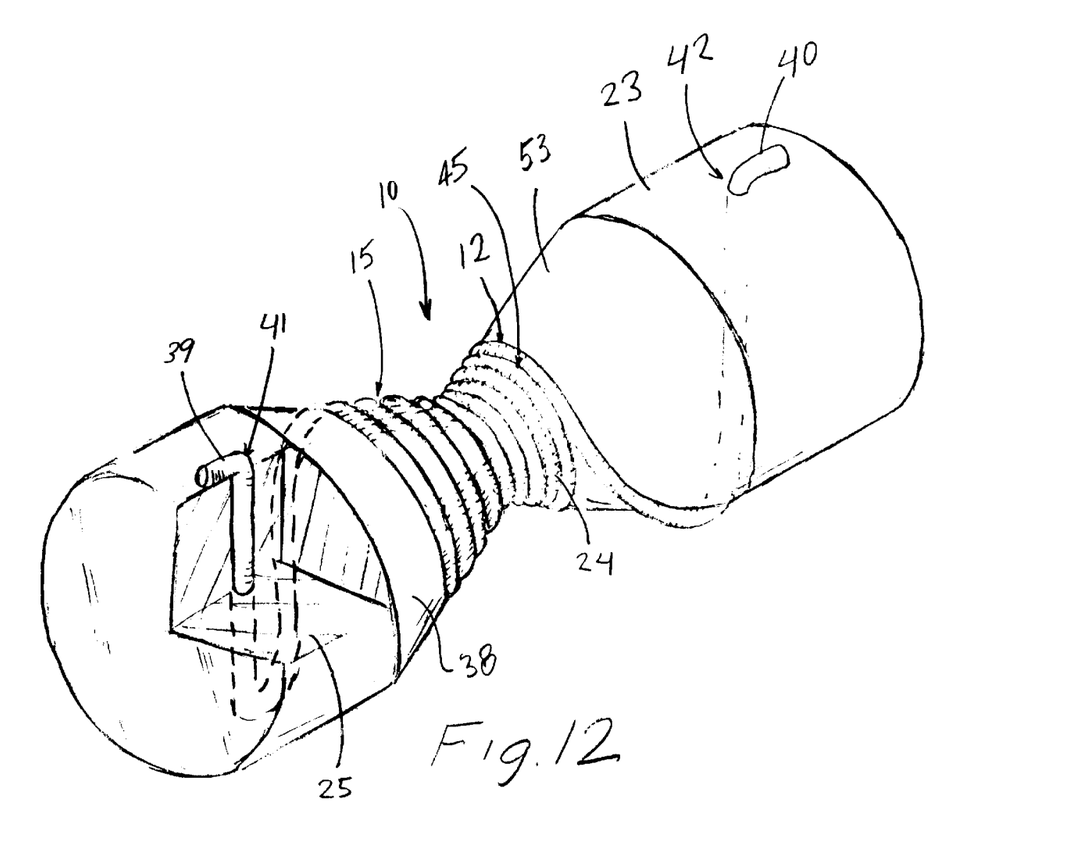
FIG. 12 depicts the longitudinally extending coil of the embolization coil of FIG. 9 wound around the tapered surfaces of a mandril that increase in opposite directions to form the conically helically shaped coils of the embolization coil.

FIG. 12 depicts conically helically shaped coils 15 and 45 of embolization coil 10 of FIG. 9 wound around respective longitudinally tapered surfaces 38 and 53 of mandril 23. The tapered surfaces 38 and 53 form a V-shaped recess that diametrically increase in opposite directions to form conically helically shaped coils 15 and 45 of the embolization coil. Ends 39 and 40 of the longitudinally extending coils are positioned through respective transverse mandril holes 41 and 42 and bent to fixedly position the coils around longitudinally tapered surfaces 38 and 53. Mandril 23 comprises material 25 such as stainless steel that is heated treated along with embolization coil 10 in an oxygen free oven.

The longitudinally extending coil 12 is wound around mandril 23 so that the turns of conically helically shaped coils 15 and 45 are in longitudinal contact with each other. Coils 15 and 45 are stress relieved and, in particular, heat treated to relieve residual stresses that are formed during the winding of longitudinally extending coil 12 and conically helically shaped coils 15 and 45. The embolization coil is heat treated in an oven as previously described. Although the embolization coil has been stress relieved, and in particular, heat treated, the turns of unrestrained coils 15 and 45 expand to a minimal spacing that increases from the minimum diameter central V-shaped notch to the larger diameter ends of the embolization coil.

Figure 10:
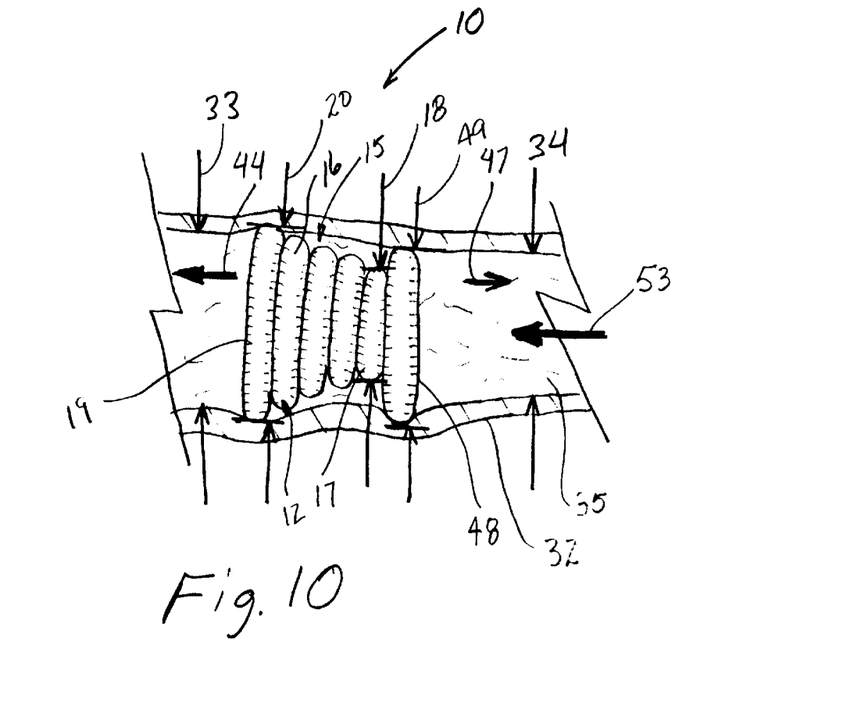
FIG. 10 depicts another alternative embodiment of the present invention in which the embolization coil includes a larger diameter end turn extending longitudinally from the minor diameter distal turn of the conically helically shaped coil.

FIG. 10 depicts another alternative embodiment of the present invention in which embolization coil 10 includes a larger diameter end turn 48 extending longitudinally from the distal turn 17 of conically helically shaped coil 15. The embolization coil is longitudinally positioned in lumen 35 of vessel 32. Although described with respect to the blood vessel of a patient, this embodiment of embolization coil 10 is readily adaptable for use in, for example, an atrial septum defect typically found in the heart of a child. This immobilization coil also includes a wire strand that has been wound into a longitudinally extending coil 12 having a plurality of tightly spaced turns. The longitudinally extending coil is wound into conically helically shaped coil 15 having a plurality of radially expanding turns 16 that expand in a first direction as indicated by arrow 44. The radially expanding turns longitudinally overlap each other and include a distal turn 17 having a minor diameter 18 and a proximal turn 19 having a major diameter 20. The longitudinally extending coil 12 is also wound into at least one end turn 48 that extends longitudinally from distal turn 17 in a second direction indicated by arrow 47. The first and second directions are generally opposite to each other. End turn 48 has an end diameter 49 larger than minor diameter 18. The larger diameter end turn 48 facilitates accurate and central positioning of the embolization coil in the vessel. End turn 48 can be extended through an atrial septum defect for positioning the embolization coil 10 therein so as to affix the coil during the occlusion of the defect. In this particular embodiment, the flow of blood as indicated by arrow 53 engages the smaller distal turn 17 of the embolization coil to cause longitudinal contact of turn 16 with each other.

The formation of embolization 10 of this embodiment coil is formed and heat treated with, for example, the mandril of FIG. 5. End turn 48 is formed with a spirally shaped disk positioned at the end of tapered surface 38. The selection of materials for the mandril and embolization is as previously described.

FIG. 11 depicts yet another alternative embodiment of the present invention in which embolization coil 10 includes a proximal end turn 50 extending longitudinally from the proximal turn 19 of radially expanding turns 16. End turn 50 extends from conically helically shaped coil 15 at a diameter 51 no greater than major diameter 20 of proximal turn 19 of the conically helically shaped coil. The embolization coil 10 is longitudinally positioned in lumen 35 of a patient vessel 32. Radially expanding turn 16 longitudinally overlap each other and include distal turn 17 having minor diameter 18 and a proximal turn 19 having a major diameter 20. Longitudinally extending coil is also wound to include proximal end turn 50 so as to provide a better anchor for the embolization coil or even more end turns of the coil for engaging the vessel wall. As a result, the radially expanding turns 16 of the embolization coil longitudinally contact each other in response to blood flowing as indicated by arrow 52 thereagainst to occlude a vessel or site in which the embolization coil is positioned. The formation and heat treatment of the embolization coil of FIG. 11 is performed using the mandril of FIG. 4 as previously suggested. The proximal end turn or turns having a diameter no greater than that of the conically helically shaped coil are formed by providing a shoulder in tapered surface 38 for winding end turns 50 therearound.

It is to be understood that the above-described embolization coil is merely an illustrative embodiment of the principles of this invention and that other heat treated or stress relieved embolization coils may be devised by those skilled in the art without departing from the spirit and scope of this invention. Furthermore, other conically helically shaped coils with spacing that increases proximally between the radially expanding turns of the coil may also be devised by those skilled in the art without departing from the spirit and scope of the invention. Although the embolization coil has been stress relieved by way of a heat treatment process, other stress relieving treatment processes are contemplated, such as through mechanical, chemical, or electrical processes.

What is claimed is:

1. An embolization coil (10) comprising:

a wire strand (11) wound into a longitudinally extending coil (12) having a plurality of tightly spaced turns (13), said longitudinally extending coil wound into a first conically helically shaped coil (15) having a first plurality of radially expanding turns (16) expanding in a first direction (44) and into a second conically helically shaped coil (45) having a second plurality of radially expanding turns (46) expanding in a second direction (47) generally opposite to said first direction (44), the turns of at least one of said first and said second plurality of radially expanding turns longitudinally overlapping each other, whereby the turns of said at least one of said first and said second plurality of radially expanding turns longitudinally contact each other in response to blood flowing therethrough to occlude a vessel in which the embolization coil is positioned.

2. The embolization coil of claim 1, wherein said first and said second conically shaped coil is heat treated to relieve stresses that are formed when winding said longitudinally extending coil and said first and said second conically helically shaped coil.

3. The embolization coil of claim 1, wherein said wire strand is comprised of a metallic alloy and wherein conically helically shaped coil is formed by the steps of: winding said longitudinally extending coil around a longitudinally tapered mandril (23) that increases in diameter in opposite directions with a plurality of turns (16, 46), heating said first and said second conically helically shaped coil when wound around said longitudinally tapered mandril at a stress relief temperature of said metallic alloy for a first time period, and cooling said conically helically shaped coil when wound around said longitudinally tapered mandril from said stress relief temperature for a second time period greater than said first time period.

4. The embolization coil of claim 3, wherein the steps of forming said first and said second conically helically shaped coil further include selecting said longitudinally tapered mandril of a material (25) that remains substantially free of surface oxidation during heating and cooling of said first and said second conically helically shaped coil.

5. The embolization coil of claim 3, wherein said metallic alloy comprises at least one from a group consisting of platinum, stainless steel, iridium, palladium, tungsten, and gold.

6. The embolization coil of claim 1, wherein said first and said second conically helically shaped coil is heated at a stress relief temperature of said continuous wire strand for a first time period and then gradually cooled down from said stress relief temperature for a second time period greater than said first time period.

7. The embolization coil of claim 1, wherein said wire strand comprises a metallic material (22) that is substantially free of surface oxidation.

8. The embolization coil of claim 1, further comprising thrombogenic fibers (26) positioned in said plurality of tightly spaced turns of said longitudinally extending coil.

9. An embolization coil (10) comprising:

a wire strand (11) wound into a longitudinally extending coil (12) having a plurality of tightly spaced turns (13), said longitudinally extending coil wound into a conically helically shaped coil (15) having a plurality of radially expanding turns (16) expanding in a first direction (44), said plurality of radially expanding turns longitudinally overlapping each other and including a distal turn (17) having a minor diameter (18) said longitudinally extending coil (12) being also wound into at least one end turn (48) extending from said distal turn of said plurality of radially expanding turns in a second direction (47) generally opposite to said first direction and having an end diameter (49) larger than said minor diameter, whereby said radially expanding turns longitudinally contact each other in response to blood flowing therethrough to occlude a site in which the embolization coil is positioned.

10. The embolization coil of claim 9, wherein said conically helically shaped coil is heat treated to relieve stresses that are formed when winding said longitudinally extending coil and said conically helically shaped coil.

11. The embolization coil of claim 10, wherein said conically helically shaped coil is formed by the steps of: winding said longitudinally extending coil around a longitudinally tapered mandril (23) and heating said conically helically shaped coil at a stress relief temperature of said metallic alloy for a first time period and then cooling said conically helically shaped coil down from said stress relief temperature for a second time period greater than said first time period.

12. The embolization coil of claim 9, wherein said conically helically shaped coil is formed by the steps of: winding said longitudinally extending coil around a longitudinally tapered mandril (23) with a plurality of turns (16) and heat treating said conically helically shaped coil when wound around said longitudinally tapered mandril to relieve residual stresses formed therein.

13. The embolization coil of claim 12, wherein the wire strand comprises a metallic alloy, the metallic alloy comprises at least one from a group consisting of platinum, stainless steel, iridium, palladium, tungsten, and gold.

14. The embolization coil of claim 9, wherein the wire strand comprises a metallic alloy, the metallic alloy includes at least one from a group consisting of platinum, stainless steel, iridium, palladium, tungsten, and gold.

15. An embolization coil (10) comprising:

a wire strand (11) wound into a longitudinally extending coil (12) having a plurality of tightly spaced turns (13), said longitudinally extending coil wound into a conically helically shaped coil (15) having a plurality of radially expanding turns (16), said plurality of radially expanding turns longitudinally overlapping each other and including a distal turn (17) having a minor diameter (18) and a proximal turn (19) having a major diameter (20), said longitudinally extending coil being also wound into at least one proximal end turn (50) extending from said first proximal turn and having an end diameter (51) no greater than said major diameter, whereby said radially expanding turns longitudinally contact each other in response to blood flowing against to occlude a site in which the embolization coil is positioned.

16. The embolization coil of claim 15, wherein the end diameter of said at least one proximal end turn is less than said major diameter of said proximal turn.

17. The embolization coil of claim 15, wherein said conically helically shaped coil is heat treated to relieve stresses that are formed when winding said longitudinally extending coil and said conically helically shaped coil.

18. The embolization coil of claim 15, wherein said conically helically shaped coil is formed by the steps of: winding said longitudinally extending coil around a longitudinally tapered mandril (23) with a plurality of turns (24) and heat treating said conically helically shaped coil when wound around said longitudinally tapered mandril to relieve residual stresses formed therein.

19. The embolization coil of claim 15, wherein the wire strand comprises a metallic alloy, the metallic alloy includes at least one from a group consisting of platinum, stainless steel, iridium, palladium, tungsten, and gold.

20. The embolization coil of claim 15, wherein said conically helically shaped coil is formed by the steps of: winding said longitudinally extending coil around a longitudinally tapered mandril (23) and heating said conically helically shaped coil at a stress relief temperature of said metallic alloy for a first time period and then cooling said conically helically shaped coil down from said stress relief temperature for a second time period greater than said first time period.

* * * * *